United States Patent [19]

Masuda et al.

[11] Patent Number: 4,555,180
[45] Date of Patent: Nov. 26, 1985

[54] PRINTED AREA MEASURING APPARATUS

[75] Inventors: Tatsunosuke Masuda, Kyoto; Tetsuo Hohki, Ibaragi; Yasuo Kurusu, Otsu, all of Japan

[73] Assignee: Dainippon Screen Mfg. Co., Ltd., Kyoto, Japan

[21] Appl. No.: 476,628

[22] Filed: Mar. 18, 1983

[30] Foreign Application Priority Data

Apr. 3, 1982 [JP] Japan .................................. 57-55670

[51] Int. Cl.⁴ ............................................ G01N 21/55
[52] U.S. Cl. ..................... 356/445; 250/559
[58] Field of Search ............... 356/243, 380, 432, 433, 356/434, 435, 443, 444, 445; 250/559, 562, 571, 572

[56] References Cited

U.S. PATENT DOCUMENTS

| 3,829,222 | 8/1974 | Aslund | 356/444 |
| 3,832,070 | 8/1974 | Cox | 356/445 |
| 3,853,409 | 10/1974 | Gaillochet | 356/432 |
| 3,958,509 | 5/1976 | Murray et al. | 250/559 X |
| 4,210,818 | 7/1980 | Green et al. | 356/444 X |
| 4,239,393 | 12/1980 | Tobias | 356/407 |
| 4,441,819 | 4/1984 | Takeuchi et al. | 356/445 X |

FOREIGN PATENT DOCUMENTS

3029273 2/1981 Fed. Rep. of Germany.
207808 12/1982 Japan.

Primary Examiner—Vincent P. McGraw
Assistant Examiner—S. A. Turner
Attorney, Agent, or Firm—Brumbaugh, Graves, Donohue & Raymond

[57] ABSTRACT

An improved apparatus for measuring the printed area of a printing plate upon which a printing image is formed, of the type having a movable scanning head provided with longitudinally arranged light sources and plural photosensors arranged in parallel with the light sources. The improvement is composed of a proving sensor device separate from and movable independently of the scanning head which includes at least one light source and photosensor. The proving sensor device provides calibration data for correcting the measurements made by the scanning head. It does this by measuring the intensity of reflected light from a totally dark printing area and a non-printing area from anywhere on the printing plate, and a totally reflective surface and totally absorptive surface, which are preferably located apart from the printing plate. The improvement further includes control means for electronically processing the measurement data produced by both the scanning head and proving sensor device.

2 Claims, 10 Drawing Figures

PRINTED AREA MEASURING APPARATUS

BACKGROUND OF THE INVENTION

The invention relates to an apparatus for measuring the area (i.e. printing area) of portions of a printing plate to which ink is applied during a printing process the measurement being carried out before the printing process so as to previously adjust the ink quantity fed to said printing plate.

The printing machines such as lithographic offset press have generally plural devices (so-called "ink fountains") that are adapted to control the ink supply rates and are disposed in a direction rectangular to the rotational direction of a printing plate attached to said machines. At initiation of the printing process, an operator should adjust the ink supply rate with regard to each ink formation by controlling the opened extent thereof so that an optimum lateral distribution of the ink quantity can be attained. In other words, the ink quantity distribution has hitherto been adjusted manually be the operator so as to avoid any excess or shortage in respect of each lateral portion of the printing plate formed thereon with an irregular pattern of figures that are to be printed on papers or the like. Such adjustment of ink fountains takes however a comparatively long period of time. Moreover, it is very difficult even for a skilled operator to exactly adjust the ink supply rates of all the ink fountains.

It has, therefore, been required to execute the initial adjustment more quickly and more accurately by any reasonable or convenient means in order to shorten the time in making necessary preparations for printing process as well as to reduce the paper loss in such adjustment work. To this purpose, it would be effective to previously measure the area of residual photosensitive layer on the printing plate such as a lithography plate. Said area of the printing plate is an image or picture portion thereof which is to be supplied with the ink, and the area will hereinafter be called "printing area". Some apparatuses have already been developed to meet the abovesaid requirement and a few of them are now used practically.

One of the known measuring apparatuses utilizes a television camera as disclosed in the U.S. Pat. No. 3958509 while in the other known apparatuses an optical system comprising some lenses is combined with photosensor elements as shown in the Japanese Early Publication Gazette (Patent) No. Sho. 50-17278 and the U.S. Pat. No. 4239393. These known systems are however not so advantageous in view of a wide variety in the size of printing plates because the size of optical system or the range of vision (or the resolving power) of said camera should be great enough to measure the biggest plate having for instance a width of more than 1 meter as well as a length of more than 1 meter. Besides such great dimension of the apparatus, a higher degree of precision will also be needed in designing such apparatuses thereby resulting in a higher cost in manufacture thereof.

Figure 1:
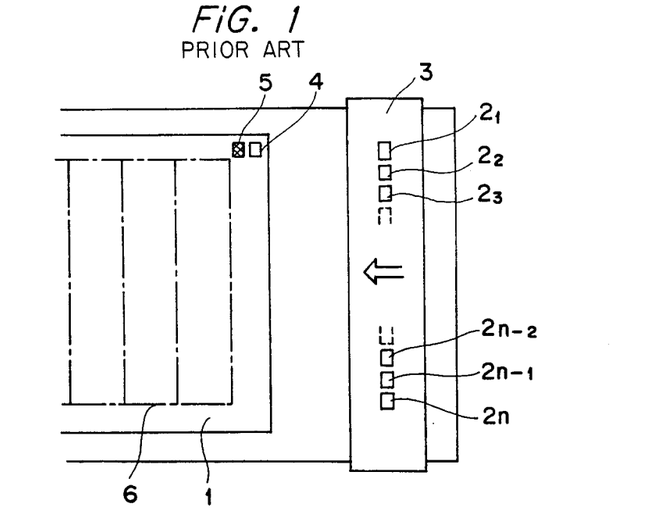
FIG. 1 is a plan view of a known apparatus for measuring a printing area.

To solve the above problems, there is proposed a simpler and less expensive apparatus as schematically shown in FIG. 1. This apparatus does not include any complicated optical system of lenses but has a photoelectric scan head 3 comprising beam sources of light (not shown) illuminating a printing plate 1 and a row of photosensors $2_1, 2_2 \ldots 2_n$ respectively disposed in the head relative to each of said sources. According to this intricate apparatus, intensities of the light beams reflected by the printing plate 1 are photoelectrically measured to determine the printing area of said plate. An example of such apparatus is disclosed in the prior Japanese Patent Application No. Sho. 56-93208 (hereinafter called "J.P.A.56-93208") in the name of the applicant of the present application.

In a practical use of such photoelectric apparatus, a calibration is indispensable to obtain correct data of the printing area. The calibration factor may in turn be obtained by testing output levels of the photosensors sensing on one hand the printing plate portion having a "printing area ratio" of 0% and on the other hand the portion having said ratio of 100%. The above "printing area ratio" is defined as a quotient of the "printing area" divided by a unit area including same wherein said "printing area" per se has the meaning as mentioned above. The so-called "calibration mark" or "100% patch" (hereinafter called "calibration mark") having the printing area ratio of 100% is therefore provided at a suitable location on the printing plate in such a manner as to permit the operator to carry out the calibration of said apparatus. (Another calibration as to the printing area ratio of 0% is possible without employing any additional calibration mark because such portions having said ratio of 0% always exist near the edges of said printing plate.) For example, a further Japanese Early Publication Gazette (Patent) No. Sho. 56-24508 has disclosed a calibration mark that is provided on a printing plate and is adapted "to calibrate the measured intensities of light reflected by the upper level and the lower level." On the other hand, the aforecited apparatus in the J.P.A. 56-93208 necessitates a calibration mark on a printing plate in order to calibrate or correct the sensitivities of its plural photosensors as well as to adjust the electric gains of its amplification circuits, each of which is connected with one of the photosensors. Details of the system disclosed in the J.P.A. 56-93208 are as follows. Namely, signal levels of each photosensor are at first measured with regard to the abovesaid portion or calibration mark which respectively have the printing area ratio of 0% or 100%. (The signal levels are hereinafter called "0% signal level" and "100% signal level", respectively.) Then, the 100% signal level is subtracted from the 0% signal level whereby the thus obtained difference is used to calculate "ratios of actual signal insensities" to said difference during measurement of the printing area ratios described hereinbefore. Thus, the sensitivities of each photosensors are calibrated simultaneously with said measurement.

Figure 2:
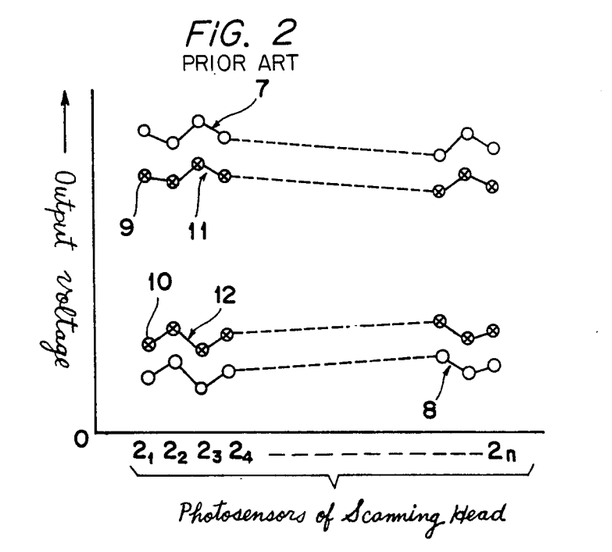
FIG. 2 is a graph showing actual output voltages along with calculated voltages corresponding to each photosensors of the apparatus.

To put it concretely, an absolutely reflective (white) portion and an absolutely absorbent (black) portion or calibration mark thereof should preliminarily be measured with all the photosensors. Said portion and said mark are uniform in their reflective character over their whole range. FIG. 2 illustrates a series of output voltages for the white portion at 7 together with another series of output voltages for the black mark at 8, respectively with regard to each photosensors $2_1, 2_2 \ldots 2_n$. One of the sensors, for instance $2_1$, is thereafter selected to be a representative sensor which should measure the intensities of beam reflected by the white portion and the black calibration mark. The thus obtained 0% signal level and 100% signal level are shown in the FIG. 2 at 9 and 10. As to remaining photosensors $2_2$ through $2_n$, said signal levels 11 and 12 are calculated by means of the above data shown at 7 through 10. It will now be apparent that such an apparatus shown in J.P.A. 56-93208 requires a printing plate formed with a calibration mark having the printing area ratio of 100%, in a manner as exemplified in FIG. 1.

In general, almost all the known apparatuses inclusive of the just described one do utilize such (a) calibration mark(s) formed on the printing plate and having said ratio(s) of 100% (and 0%). This will result in a complication and a poor productivity in the plate making process.

BRIEF SUMMARY OF THE INVENTION

A primary object of the invention is therefore to provide a printing area measuring apparatus that does not need any calibration mark formed on a printing plate.

Another definite object is to provide a printing area measuring apparatus with a separate photosensor device independent from a row of ordinary photosensors carried by a scan head, the separate photosensor device being capable of sensing arbitrary portions or zones within the printing plate and on the exterior thereof in order to calibrate the ordinary photosensors.

Still another object is to construct a printing area measuring apparatus provided with a separate photosensor device that is freely movable independent of a set of ordinary sensors of a scan head while it being electrically connected to a common control circuit adapted to an electronic date processing for calibration of the ordinary sensors as well as for measurement of the printing area of a printing plate.

By the invention, a necessity for a calibration mark on the printing plate will be excluded thereby remarkably improving the productivity in the plate making step of printing process. The separate photosensor device will hereinafter called "proving sensor device".

Other objects and merits will be made clear in the following description of an embodiment.

DETAILED DESCRIPTION OF A PREFERRED EMBODIMENT

Figure 3:
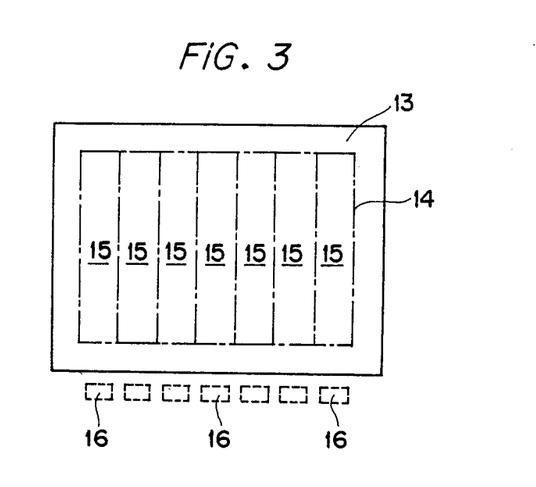
FIG. 3 is a plan view of a printing plate the printing area of which is to be measured.

A printing plate 13 is at first outlined here referring to FIG. 3 for the convenience of the following description. The plate 13 may be any arbitrary plate such as that used in the lithographic press. The printing area of said plate is measured by the apparatus described hereinafter and has a image zone 14 where an image has been developed. The reference numeral 15 within phantom rectangles designates divisions of said zone 14 which are not physically divided but only defined imaginarily in a direction in which a plate cylinder of the printer rotates. Said divisions 15 are in parallel with one another and respectively supplied with ink from one of ink fountains 16 independently from each other.

Adjustment and control of the ink feeding rates of each ink fountain is of decisive importance for achievement of a good printing performance.

Residual photosensitive layers, which ar remaining attached on said divisional zones 15 after a develope process in plate making, are the printing areas (or ratios thereof) that are to be measured by using the invented apparatus. A photo-absorption method may be utilized for this purpose. For example, a pre-sensitized plate produced by the FUJI SHASHIN FILM Co. Ltd., gives a dark green color to the residual photosensitive layers so that the areas of the latter are conveniently measured by means of red light which is intensively absorbed by said color.

Figure 4:
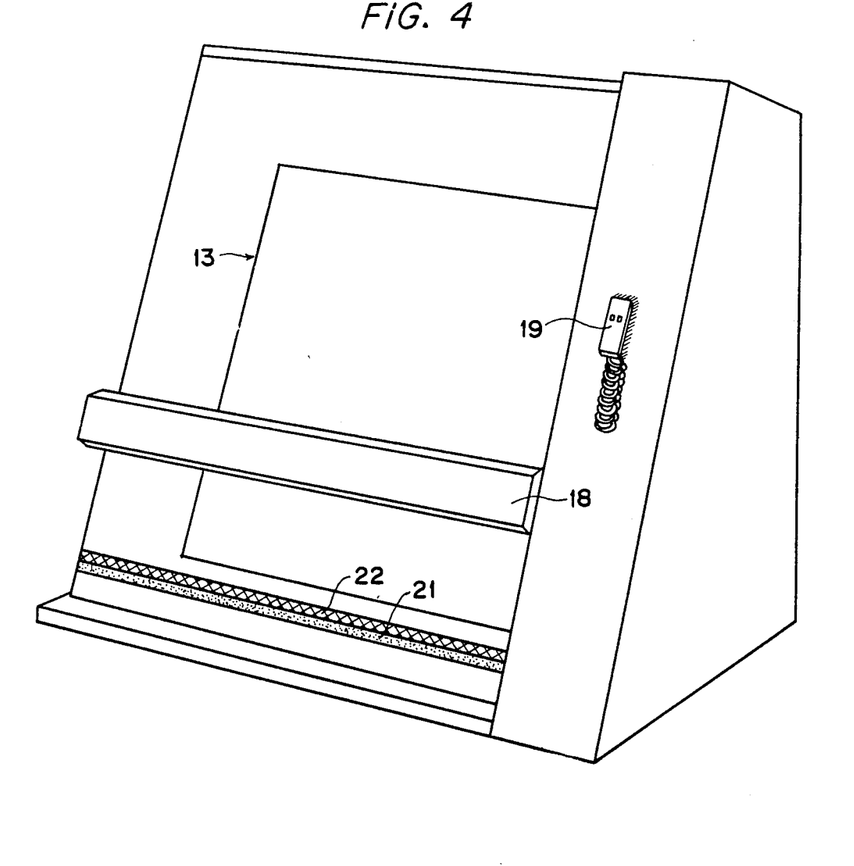
FIG. 4 is a perspective view of an apparatus in accordance with an embodiment of the invention.

Referring now to FIG. 4, the printing plate 13 is mounted to the illustrated apparatus. The reference numeral 18 indicates a scanning head comprising plural photosensors $17_1$, $17_2$ ... $17_n$ and plural beam sources of light. The apparatus also includes a proving sensor device 19 separate from the scanning head and comprising also a photosensor $17_o$ as well as a light source therefor. The details thereof will be described below. Designated at 21 and 22 are an absolutely reflective (white) zone and an absolutely absorptive (black) zone located outwardly of the printing plate 13.

It will be appreciated that the apparatus further comprises a microcomputer or any other suitable central processing unit (CPU) within its interior and that the relative movement of the plate 13 and the head 18 may be caused in a different manner from that suggested in FIG. 4 in which the plate 13 stands stationary.

Figure 5:
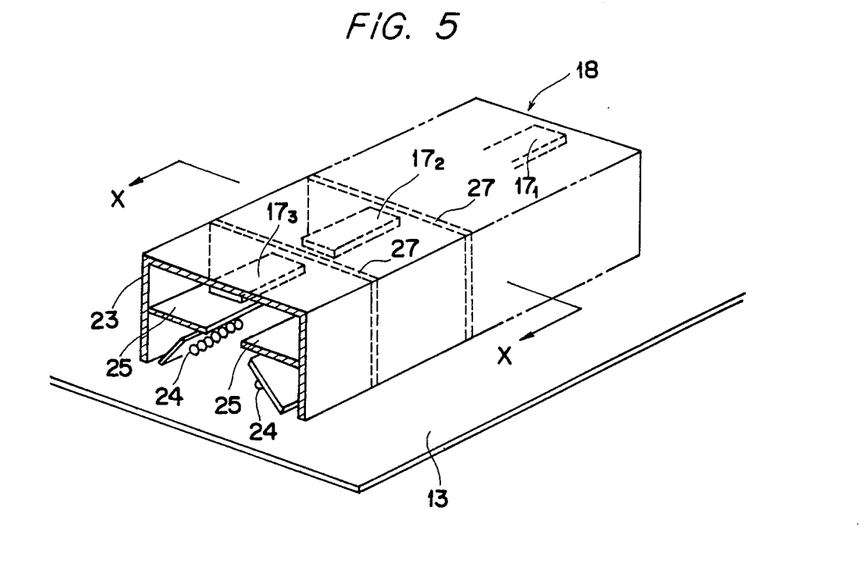
FIG. 5 illustrates a scanning head, with a partly sectional view, incorporated into the invented apparatus.
Figure 6:
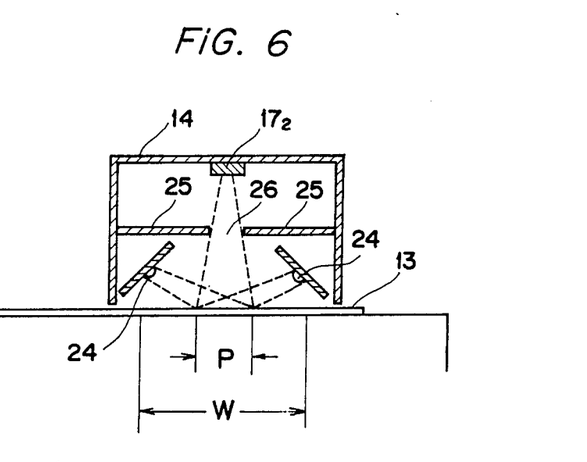
FIG. 6 is a cross section along the line X—X in FIG. 5.

As seen from FIGS. 5 and 6, the scanning head 18 comprises plural sources 24 of beams of light that are arranged in a row within a casing 23. These beam sources irradiate a light of proper wave length and may be light emitting diodes (LED), sodium lamps, fluorescent lamps or the like. Masking plates 25 are disposed between the beam sources 24 and the photosensors $17_1$ to $17_n$. The plates 25 prevent the beams of light reflected by non-predetermined regions of the plate 13 from passing through a slit 26 to the photosensors. Partitions 27 are also interposed between each two photosensors to protect same from the neighboring beam sources so that each photosensor can receive only the light beams emitted by its own source. Said photosensors are aligned into a line parallel to the plate which line in turn is in a vertical alignment with the slit 26 between the plates 25 in the direction normal to the surface of said printing plate 13.

Figure 7:
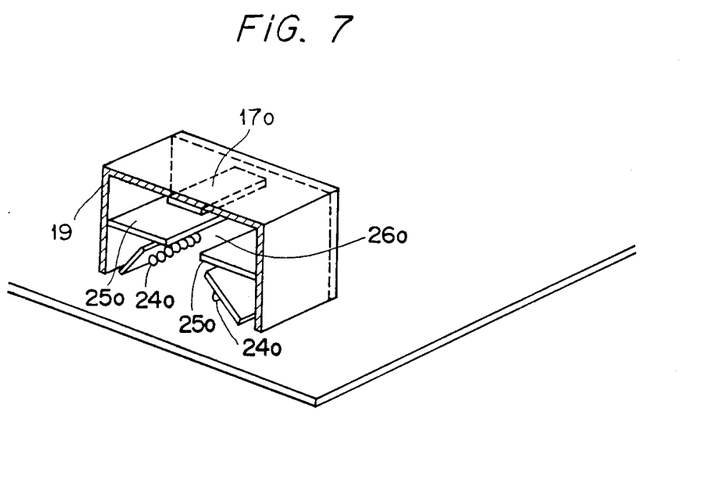
FIG. 7 is a perspective view of a proving sensor device also incorporated into the invented apparatus.

A structure of the aforementioned proving sensor device 19 is illustrated in FIG. 7. This device 19 comprises plural light beam sources $24_o$, masking plates $25_o$, a slit $26_o$ formed between the latter as well as a single photosensor $17_o$, all these members being disposed within a casing in a manner similar to the scanning head 18. It is preferable that the sources $24_o$ and the photosensor $17_o$ have the same characteristics as those in the head 18. However, a usual photometer may be used in place of such a device 19 of special structure as far as the photometer can scan and measure the printing plate 13 and the white and black zones 21, 22.

In operation of the above apparatus, the scanning head 18 will be positioned in parallel to the belt-shaped divisional zones 15 in such a manner that the entire length of the latter can be photoelectrically measured by means of the photosensors $17_1$ to $17_n$. The head 18 is caused to move over the printed zone 14 in a direction perpendicular to the direction in which each divisional zone 15 extends to thereby measure the printing areas (or ratios thereof) of said zones respectively corresponding to each ink fountain 16.

Giving a full detail of the principle of measuring operation, the width (P) (i.e. a partial width of each divisional zone 15 in a direction perpendicular to the extending direction of said zones shown in FIG. 3) which can be measured by photosensors 17 at each step of intermittent movement of the scanning head 18 is determined by the width of the slit between the masking plates 25. Therefore, such measurement of the reflected light intensities from the partial width (P) will be repeated several times until the sum of said widths becomes the entire width (W) of one divisional zone 15 in the whole zone 14 during the stepwise movement of said scanning head 18. Thus, the printing area (or ratio thereof) is obtained for the one divisional zone and thereafter such measurement will be carried out again for the successive zones 15 while causing the head 18 to move in a direction perpendicular to that in which said zones 15 extend. It is recognized, of course, that a decrease of the unit width (P) to a smaller width P/a (wherein a is a positive integer) will improve the accuracy of the measurement.

The present invention does not reside in the above principle but resides in the following calibration mechanism. Namely, the sensitivities of said plural photosensors $17_1$ to $17_n$ and amplifying circuits connected thereto are conveniently executed in a manner described below.

Figure 8:
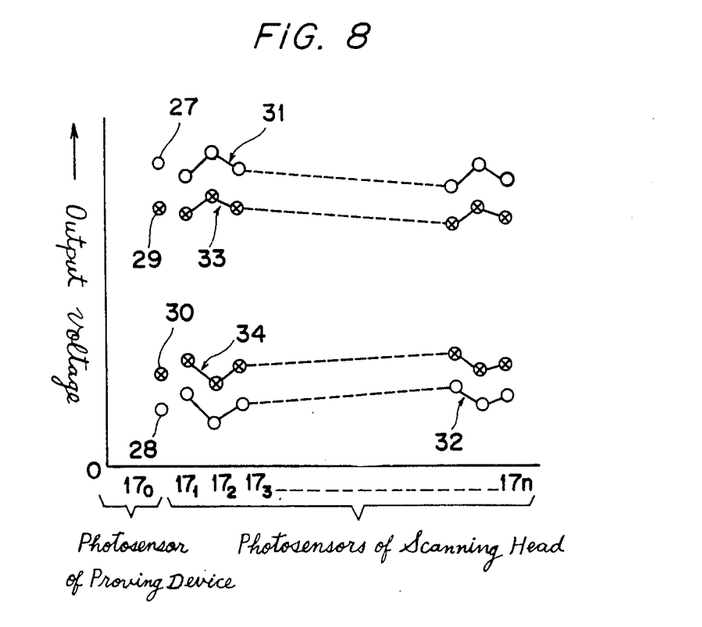
FIG. 8 is a graph indicating actual and calculated output voltages of all the sensors inclusive of those built in the scan head.

An operator attending the above apparatus should at first operate the proving sensor device 19 in order to test the white zone 21 and the black zone 22 to thereby obtain respectively a white level signal 27 and a black level signal 28 shown in FIG. 8. Next, he operates also the device 19 for obtaining a 0% signal level 29 as well as a 100% signal level 30 wherein he causes the device to sense respectively a non-printing portion and an image printing portion forming an image such as a line, character or picture.

After the abovesaid preliminary operation, the operator will then cause the scan head 18 to move and sense the white and black zones 21 and 22. White level signals 31 and black level signals 32 are thus produced as shown in FIG. 8 with regard to all the photosensors $17_1$, $17_2 \ldots 17_n$ incorporated within the head 18. Using these data 27, 28, 29, 30, 31 and 32, the central processing unit in the control device will automatically compute the 0% and 100% signal levels 33, 34 as well as the differences between them for each photosensor $17_1 \ldots 17_n$. The differences are preferably stored in a memory of the control device. As the scanning head advances and scans the divisional zone 15, actual output voltages which fall in the ranges between the data 33 and 34 are produced and the data 34 are automatically subtracted from said voltages. The thus obtained differences will then divided by the foregoing referential differences between the data 33 and 34 to thereby give quotients. The quotients are summed up by the control device so as to provide reasonable measures for adjustment of ink feed rates.

Figure 9:
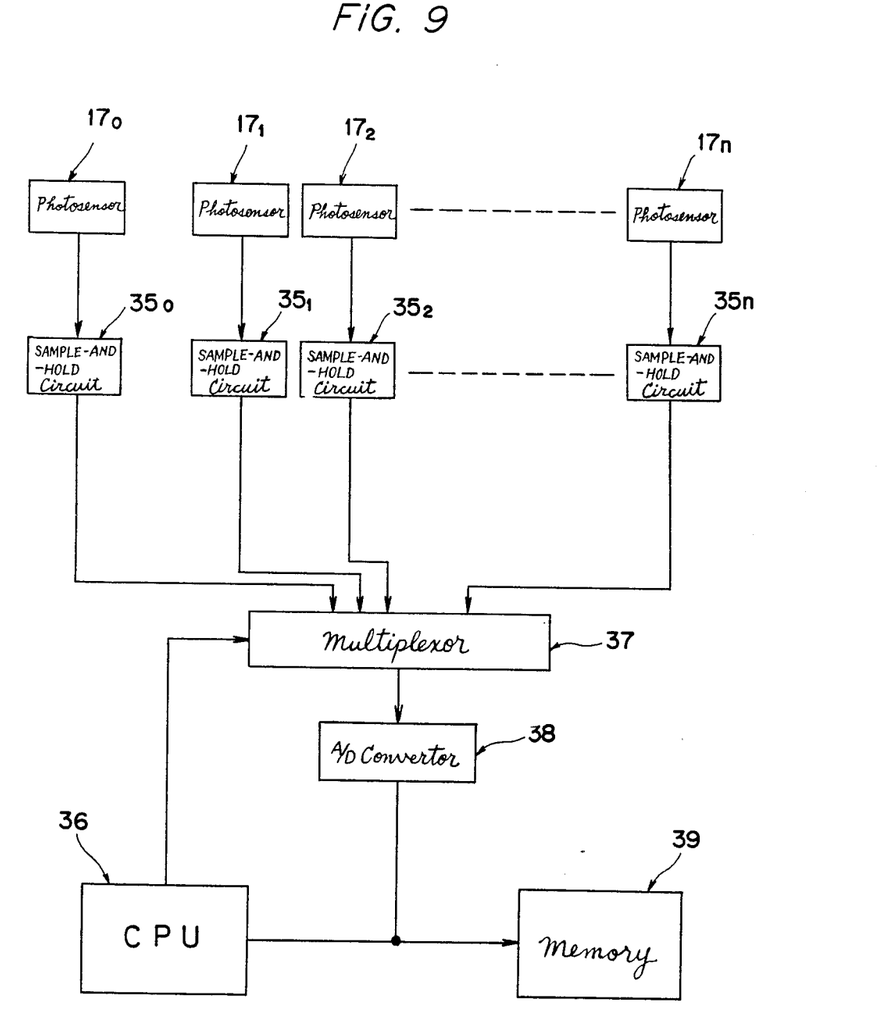
FIG. 9 is a block diagram of an electronic data processing system utilized in the invention.

In the next place, an example of the data processing system will be made clear with reference to FIG. 9. When the photosensors $17_o$, $17_1$ to $17_n$ receive reflected beams of light, they produce output voltages in proportion to the intensities of the light which they received. According to the command signal from the CPU 36, the voltages which are respectively retained transiently in SAMPLE-AND-HOLD circuits $35_0$, $35_1$ to $35_n$ are then discharged therefrom and fed in sequence to an analog-to-digital (A/D) convertor 38 via a multiplexor 37. Digitized signals are written into a memory device 39 each at predetermined addresses. This processing mode is common to all the data produced by the scanning head 18 and the proving device 19. Each sensor has its own address in the memory 39 so that when the head 18 measures the image zone 14 the plural output signals from any one of the photosensors 17, to $17_n$ are accumulated at its own address during a measurement of one divisional zone 15 in said zone 14. Thus, the printing area (or ratio thereof) can be determined very easily for each divisional zone.

A display device may be adapted to indicate the final data given by CPU 36 for each zone 15 either in a graph or in a numeric table. Further, such final data may be automatically sent to the ink fountain control devices thereby enabling a direct adjustment thereof.

Figure 10:
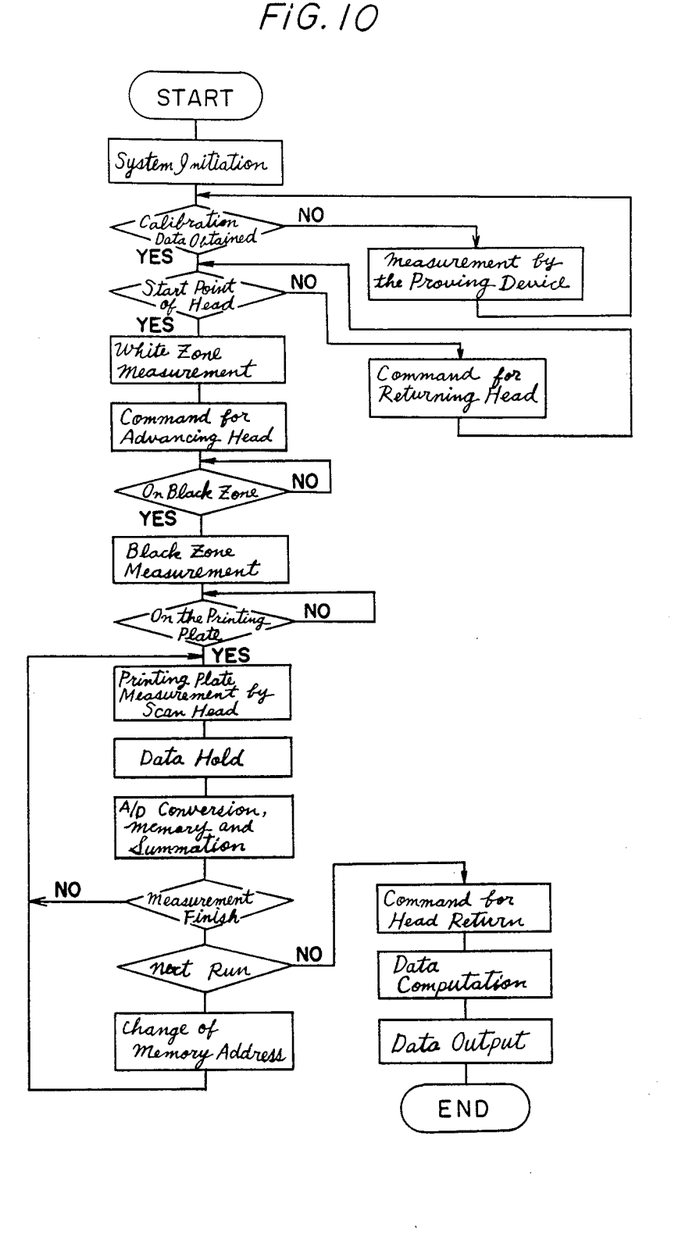
FIG. 10 is a flow chart for said system.

Giving some additional explanations, an initial setting of the control device is effected for instance by pushing a start button to thereby clear the preceding data, to switch on the sources of light beams and to reset the SAMPLE-AND-HOLD circuits 35 as shown in FIG. 10, thereafter proceeding to a decision of whether or not the calibration data have already been charged into the control device. If not, the operator is to measure using the proving device 19 the portions in printing plate having 0% and 100% values of printing area ratio and also to measure the white and black zones 21, 22 on the exterior of said plate. The next step is a decision on the position of the scanning head 18. If the head is not on the starting point, it will be returned there once and actuated then to move forward. Thus, the photosensors sense the white area 21 thereby sending the data to the memory during the movement of the head 18. As the travel of said head to the black zone 22 is detected photometrically or electrically, the measurement of said zone is executed and the data thereof are sent to the memory thereby producing the 0% and 100% signal levels for each photosensor as illustrated in FIG. 8.

After this step has finished, the scanning head 18 will move to the regular position, i.e. to the first divisional zone 15 where all the photosensors within the head 18 produce the output voltages that are then sent to and temporarily stored in the SAMPLE-AND-HOLD circuits 35. These data are subsequently read out of said circuit one by one in accordance with the multiplexor 37 so as to be converted into digital data by the A/D convertor 36 and written into the predetermined addresses of the memory 39. This process will be repeated necessary times for the first divisional zone while summing up the digitized data to thereby compute the printing area (or ratio thereof) and store it in the memory. The other succeeding divisional zones, i.e. the second zone, etc., will be scanned in the same manner. After the last divisional zone 15 has been scanned, the scan head 18 will return to the start point and the CPU 36 instructs the display device to indicate the thus-obtained printing areas (or ratios thereof) of each divisional zones.

Any known or conventional means such as those adapted to count the clock pulses from a pulse generator or to catch the coded signals from a position encoder may be employed in order to control the timing of the measurement and/or to detect the position where the scanning head must stop for the measurement.

It will be appreciated that the apparatus just described above can be modified in various manners without departing from the spirit and the scope of this invention. For example, the scanning head may be driven to move parallel with the longitudinal direction of the divisional zones 15 that are defined to be of rectangles in the image zone 14 of the printing plate 13. In use of the apparatus, the calibration procedure will not necessarily be conducted for all the printing plates in case that they have the same pattern of printed image. It will be sufficient in color printing process to calibrate the scanning head for only one of the four types of printing plates, i.e. the cyan (C) plate, the magenta (M) plate, the yellow (Y) plate and the black (BK) plate. The inverted apparatus may be used not only in the printing process but also in the plate making process. Some processing solutions in the latter process will effectively be controlled if the invented apparatus is connected directly or indirectly to the plate making apparatus.

What is claimed is:

1. An improved apparatus for measuring the printing area of a printing plate upon which a printing image area is formed of the type having a scanning head, movable in relation to the printing image area, which includes light sources arranged linearly and a plurality of photoelectric transfer elements arranged in parallel with the linear arrangement of light sources, wherein the quantity of light from said light sources reflected from said printing plate is measured by said photoelectric transfer elements during a scanning operation of said scanning head, and the data obtained by such measurement is processed to measure said printing area, the improvement comprising:

proving sensor means, separate from and movable independently of said scanning head, for measuring separately from said scanning operation a portion of said printing plate having a 0% signal level and a portion of said plate having a 100% signal level to provide calibration data for correcting the measurement of the printing area by said scanning head, said proving sensor means having at least one light source and one photoelectric transfer element.

2. An improved apparatus according to claim 1, wherein the improvement further comprises:

control means for electronically processing the data produced by both said scanning head and said proving sensor means.

* * * * *